United States Patent [19]

Useldinger et al.

[11] 4,307,608
[45] Dec. 29, 1981

[54] APPARATUS FOR DIGITALLY DISPLAYING MUSCLE STRENGTH

[75] Inventors: Ronald E. Useldinger, San Jose; Joseph E. Byerly, Santa Clara, both of Calif.

[73] Assignee: Fitness Motivation Institute of America, San Jose, Calif.

[21] Appl. No.: 112,120

[22] Filed: Jan. 14, 1980

Related U.S. Application Data

[63] Continuation of Ser. No. 859,468, Dec. 12, 1977, abandoned.

[51] Int. Cl.³ .............................................. G01L 5/02
[52] U.S. Cl. .................................... 73/379; 73/862.53
[58] Field of Search ...................... 73/379, 380, 141 R, 73/141 A, 139, 770, 862.53; 324/99 D; 272/125, 135, 137, 141, 142

[56] References Cited

U.S. PATENT DOCUMENTS

| | | | |
|---|---|---|---|
| 3,012,195 | 12/1961 | Slocomb et al. | 324/99 D X |
| 3,442,132 | 5/1969 | De Mare | 73/379 |
| 3,559,059 | 1/1971 | Martin et al. | 324/99 D |
| 3,670,573 | 6/1972 | Kroemer | 73/379 |
| 3,680,386 | 8/1972 | Cannon | 73/379 |
| 3,742,760 | 7/1973 | Kato | 73/141 A |
| 3,848,468 | 11/1974 | Richards | 73/380 |
| 3,868,848 | 3/1975 | Senour | 324/99 D X |
| 3,895,517 | 7/1975 | Otto | 73/139 X |
| 3,896,672 | 7/1975 | Henson et al. | 73/379 |
| 3,995,492 | 12/1976 | Clynes | 73/379 |
| 4,115,767 | 9/1978 | Brosh et al. | 177/DIG. 3 |
| 4,125,016 | 11/1978 | Lehoczky | 73/139 |

FOREIGN PATENT DOCUMENTS

656187  1/1963  Canada ................................ 73/379

OTHER PUBLICATIONS

Schmid-*Electronics*, Nov. 28, 1966, pp. 88-94.
Vos et al., "Telemetry of Biomechanical Forces During Exercise", pp. 279-288, May 1971.

*Primary Examiner*—Charles A. Ruehl
*Attorney, Agent, or Firm*—Harry M. Weiss

[57] ABSTRACT

This disclosure relates to an apparatus for digitally displaying muscle strength. This apparatus measures the output of a load cell under tension or compression and presents a digital readout of the force applied to the load cell in pounds. This apparatus features among other things an analog output which is linearly related to force in pounds for driving a chart recorder, a digital readout of force in pounds and a memory feature which permits retention of the peak value in pounds as a number readout until such time as the result is cancelled at the press of a button.

9 Claims, 7 Drawing Figures

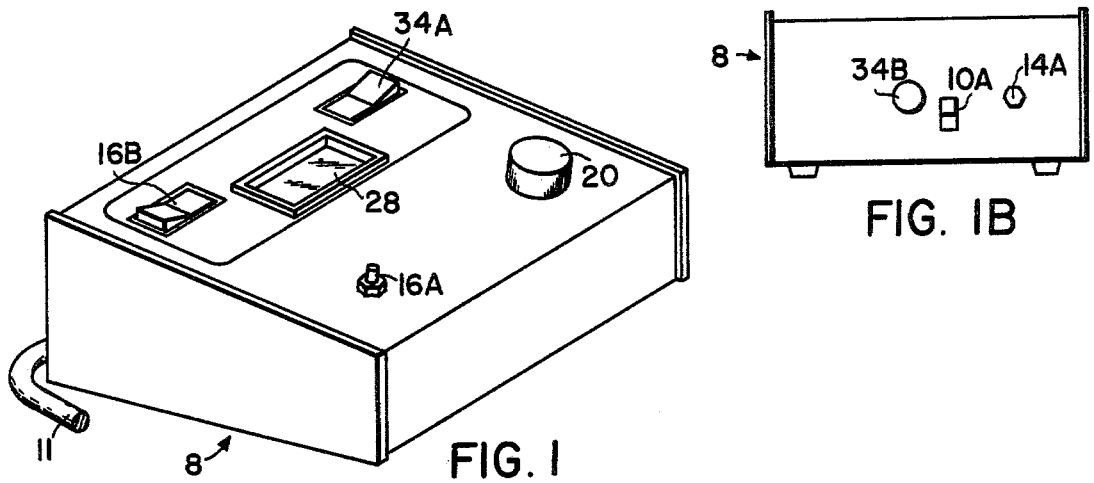
FIG. 1
FIG. 1B
FIG. 1A
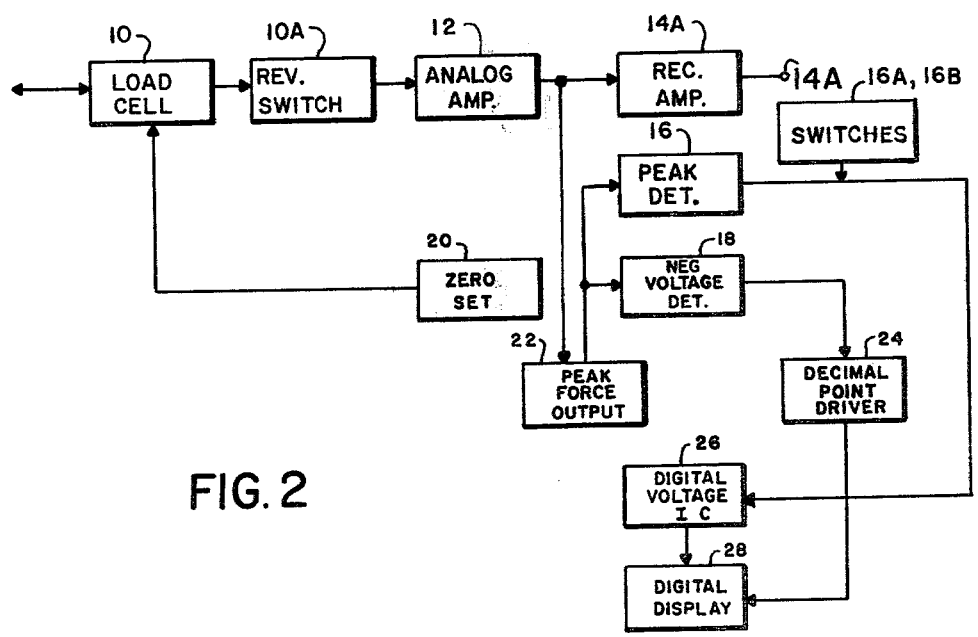
FIG. 2

4,307,608

APPARATUS FOR DIGITALLY DISPLAYING MUSCLE STRENGTH

This is a continuation of application Ser. No. 859,468, filed Dec. 12, 1977, now abandoned.

BACKGROUND OF THE INVENTION

1. Field of the Invention

This invention relates generally to electronic apparatus which utilize strain gauges installed in load cells, and more particularly, to electronic apparatus for processing of strain gauge signals to drive chart recorders and for a digital voltmeter calibrated to readout in pounds from applied muscle tension.

2. Description of the Prior Art

Load cells and associated electronic circuitry are routinely used to weigh everything from diamonds to meat to freight cars. Specialized load cells with its associated electronic circuitry have also been used in the past and are still presently being used for measurement of high static forces and torque. While load cell electronic systems have been incorporated into weighing systems designed for accurate weighing of humans, the relatively high cost of such systems has limited their adoption prior to the advent of reliable low-cost integrated circuits.

The user of the strength meter described in this disclosure applies muscle tension to an unyielding load cell unit which results in an isometric or static force measurement. This differs from a typical ergometer measurement which evaluates dynamic human effort in terms of energy. Thus, isometers involve measurement of a static force or weight without involving movement of the force or weight sensor whereas ergometers measure dynamic effort or energy which involves movement of the effort or energy sensor of the ergometer.

U.S. Pat. No. 3,995,492 issued Dec. 7, 1976 to Manfred E. Clynes describes a sound producing isometric exerciser. This is a dumb bell or dog bone shaped object, sized to fit conveniently in both hands and covered with plush fur pile or padded leatherette. By the user grasping the ends of the exerciser, the user is able to exert a compressive or tension force on a transducer coupled to a rigid link within the exerciser device. The transducer converts this applied force into a corresponding electrical value that is processed by a pulse generator and audio oscillators which are coupled to a loudspeaker housed within the structure, thereby producing a train of audible pulses whose repetition rate, tone and amplitude depend upon the applied force. Thus, the user receives a continuous sound which is maintained as long as the same level of force is applied. However, this sound can be varied by changing the applied force. By means of a "bleep" counter responsive to the audio output of the pulse generator, the user's performance is scored.

However, while this device described in U.S. Pat. No. 3,995,492 appears to be suited for indicating when an arbitrary but unknown muscle force level has been reached, as in a series of isometric exercises, it is not suitable for measurement of absolute or ultimate muscle strength in units such as pounds and provide a clear readout identifying the exact magnitude of the applied force.

U.S. Pat. No. 3,913,563 issued Oct. 21, 1975 to Newton E. Ball describes a transducer designed to function in a muscle contraction (primarily for pregnant women) monitor. Output of the transducer described in U.S. Pat. No. 3,913,563 is combined with other physiological measurements in a patient monitoring system.

Accordingly, none of the cited prior art discloses an apparatus which permits a user of the apparatus to obtain a read-out in units of force which can be used as a measurement of strength and growth of strength. Therefore, a need existed for such an apparatus to permit a user thereof to monitor strength capabilities.

SUMMARY OF THE INVENTION

Accordingly, it is an object of this invention to provide an apparatus for displaying muscle strength.

It is another object of this invention to provide an apparatus for digitally displaying muscle strength.

It is still another object of this invention to provide an apparatus for digitally displaying muscle strength which employs a strain gauge equipped load cell to convert force in both tension and compression to an electrical analog signal.

It is a further object of this invention to provide an apparatus for displaying muscle strength which uses a strain gauge equipped load cell with means to amplify the low-level output of the load cell so that each pound of applied force is represented by one milli-volt of output signal.

It is a still further object of this invention to provide a digital strength meter having a load cell wherein a digital voltmeter circuit is used which is scaled so that a one digit count of a three and one half digit readout equals one pound of force applied to the load cell.

The foregoing, and other objects, features, and advantages of the invention will be apparent from the following, more particular description of the preferred embodiment of the invention, as illustrated in the accompanying drawing.

BRIEF DESCRIPTION OF THE DRAWING

FIG. 1 is an external perspective view of the self-contained digital strength meter readout unit or apparatus of this invention.

FIG. 1A is a perspective view of the housed load cell unit that is electrically connected to apparatus of FIG. 1 showing steel actuator yokes which permit attachment of handgrips (as shown), rings, S-hooks, bars or cables (not shown) or whatever other tackle may be required for human strength evaluation.

FIG. 1B is a rear side elevational view showing the back of digital strength meter apparatus of FIG. 1.

FIG. 2 is a block diagram of a load cell of FIG. 1A with bonded strain gauges (not shown) and associated electronic circuits required to process the basic strain gauge output for the digital strength meter display of FIG. 1 and to provide an output for driving a graphic chart recorder (not shown).

THE SPECIFICATION

Figure 3A:
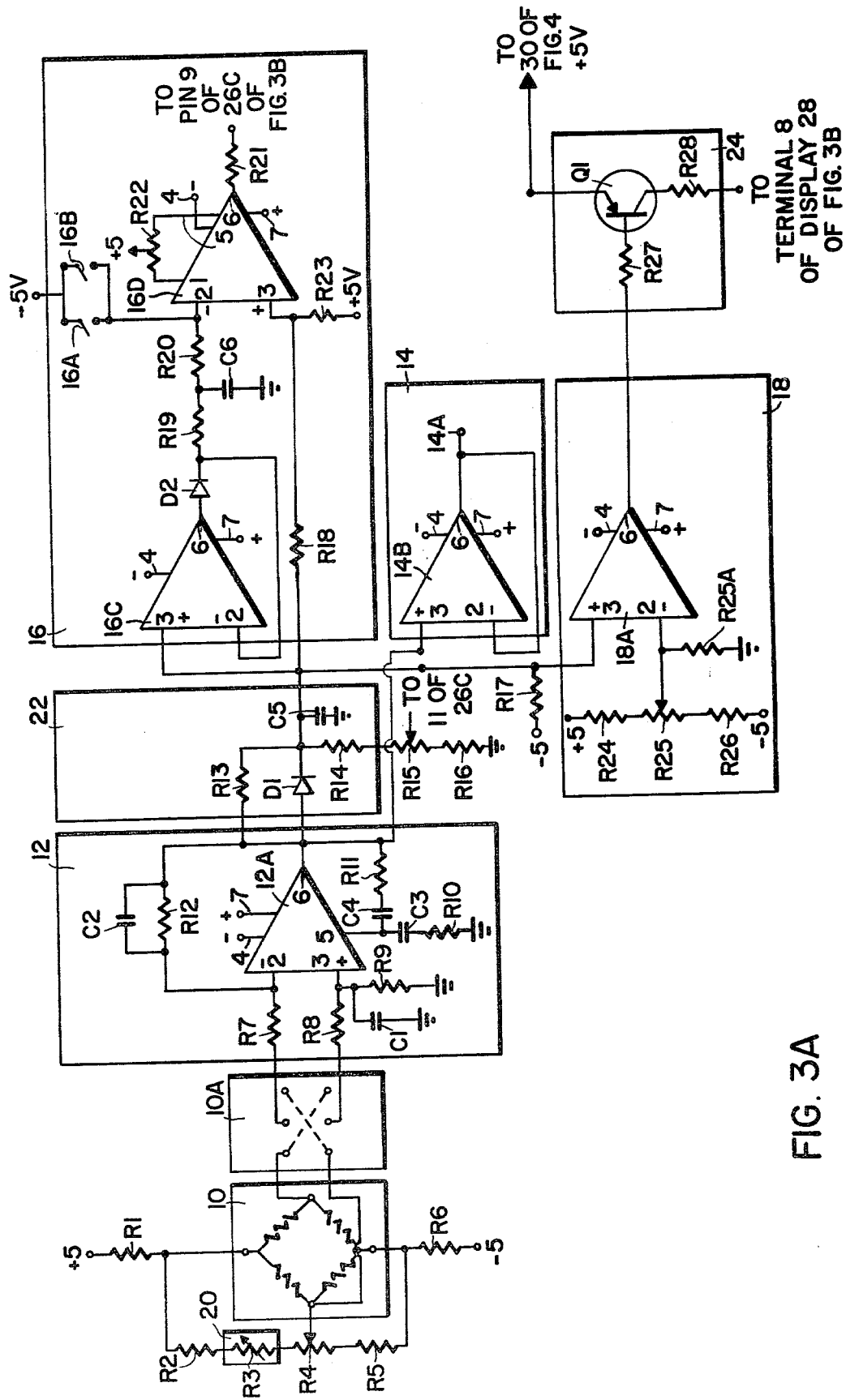
FIGS. 3A and 3B are electrical schematics which show the details of the interconnection wiring of the blocks of FIG. 2.

This disclosure describes a method of or apparatus for evaluating muscle power with special hand held tackle or gripping means coupled to a load cell or converting means driving associated electronic systems which produce a digital readout of force in pounds and, if desired, a low impedence output voltage equal to one milli-volt per pound, suitable for driving a graphic recorder.

Referring to FIG. 1, reference numeral 8 generally refers to the digital strength meter apparatus. Referring to FIG. 1A, reference numeral 10 refers to the load cell or converting means that is electrically connected to the digital strength meter apparatus 8 by means of, preferably, a four conductor cable 11. Referring to FIG. 1B, reference numeral 10A is a reversing switch which functions to reverse the sensing of the load cell 10 to generate in either a tension or compression mode, as desired. An output jack 14A is shown on the back panel (see FIG. 1B) of the digital strength meter apparatus 8 and is used for electrical connection to an analog chart recorder (not shown).

Referring to FIG. 1, push button switch 16A is used to cancel accumulated force peaks in order to permit a new series of digital strength meter readings to be initiated. Switch 16B is used to disable or enable the memory function of the digital strength meter apparatus 8 as further explained below. The memory switch 16B can be set so that the readout retention feature is not operational. This would be desirable, for example, in a series of isometric exercises where a predetermined value in pounds would be achieved on each pull. A zero setting resistor knob 20 is used to set the digital readout to zero prior to each use. A LED type readout 28 is used to designate the digital readout of the apparatus during operation. An on-off switch 34A is used to turn the power on or off for the digital strength meter apparatus 8. Referring to FIG. 1B, a line fuse 34B is used as a safety fuse in the power supply primary circuit.

Referring to FIG. 2, a block diagram is shown of the entire electric circuit of the digital strength meter apparatus 8 of FIG. 1. The functional relationship of various parts of the digital strength meter apparatus 8 of FIG. 1 is explained below. Box 10 contains a load cell which preferably has a maximum range of 1000 lbs. Thus, a person pulling on the handgrips (see FIG. 1A) can measure their strength in terms of pounds of force. The reversing switch 10A (see FIGS. 1B, 2 and 3A) facilitates upscale (forward direction only) output readings, regardless of whether the load cell 10 is in tension (pulling out on handgrips) or compression (pushing in on handgrips). The output of the load cell 10 (in milli-volts) is generated by unbalancing a conventional four-arm Wheatstone bridge. The output of the load cell 10 is fed into an analog signal amplifier 12. The output of box (analog signal amplifier) 12 is further amplified by chart recorder amplifier 14 which provides an analog electrical signal proportional to muscle force input in pounds, suitable for directly driving a graphical strip chart recorder (not shown) which will permit the operator to generate a force readout on a strip chart (not shown) as a function of time. Boxes 16 and 22 operate cooperatively to detect the peak force readings achieved during operation of the digital strength meter apparatus 8 and to hold force peaks thus generated until no longer needed for observation. Negative voltage detector 18 and decimal point driver amplifier 24, which is electrically connected to the negative voltage detector 18, together turn on the display decimal points and thereby warn of any negative bias which may be introduced by attachment of the load cell 10 to the mechanical linkages (not shown) for muscle force input. Both positive and negative bias can be corrected by adjustment of the zero setting control R3 (see FIG. 3A), which is equivalent to the knob 20 (of FIG. 1) and the box 20 of FIG. 2. The peak force output from peak detector 16 drives digital voltmeter module 26 which in turn generates the numeric parts of digital display 28 (see FIGS. 1, 2, and 3B).

Figure 3B:
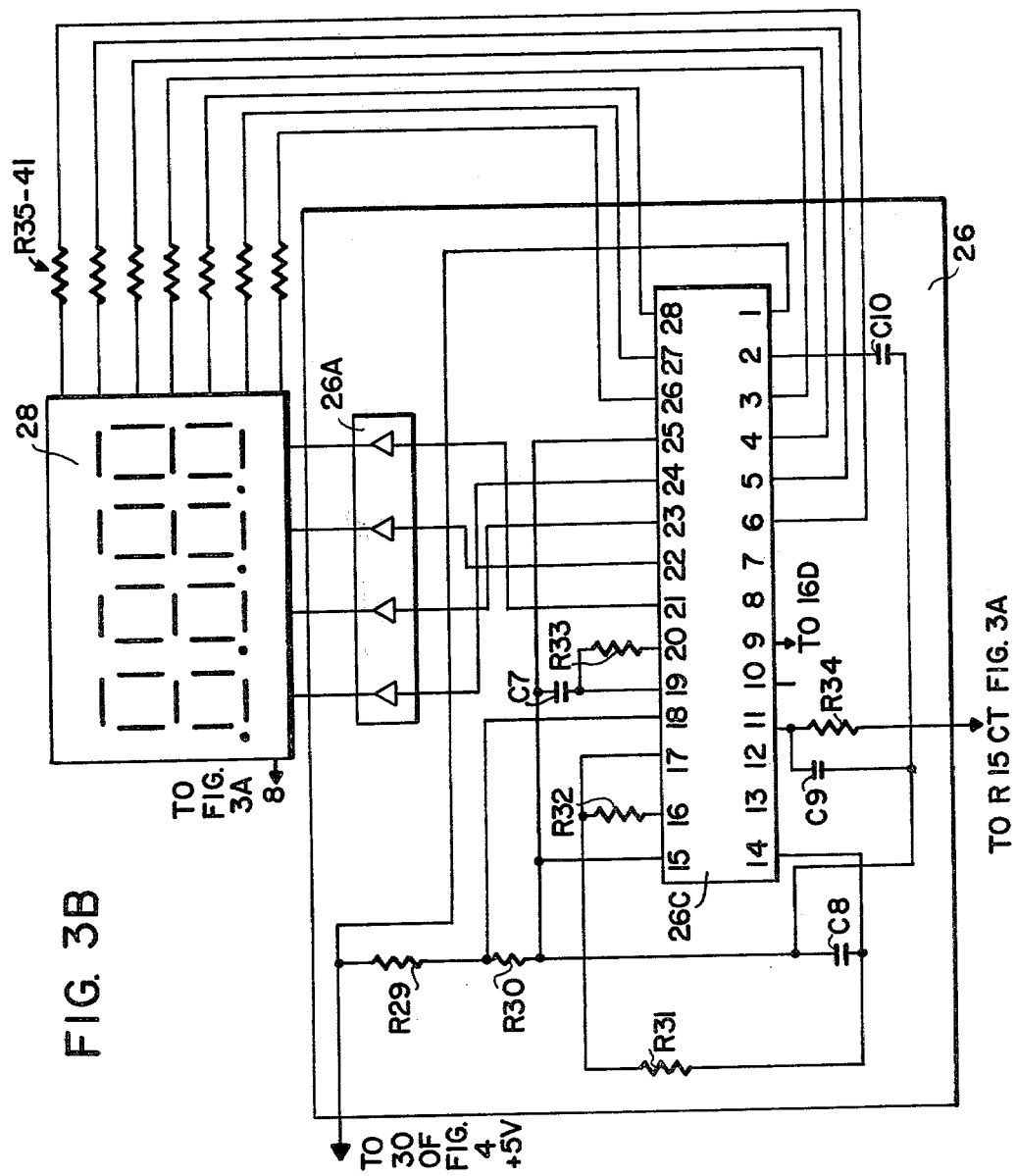

FIGS. 3A and 3B are together the electrical schematic representation of the block diagram of FIG. 2. FIGS. 3A and 3B show how the output of the load cell strain gauge transducer 10 is converted to an analog voltage and an equivalent decimal value with commercially available integrated circuits. The following integrated circuits, products of National Semiconductor Corporation, are used in the digital strength meter apparatus 8:

1 ea. LM725, an operational instrumentation amplifier with stable closed loop gain, low drift and low noise (see reference numeral 12A in box 12 of FIG. 3A).

2 ea. LF355, a monolithic JFET input operational amplifier on the same chip with standard bipolar transistors, Bi-Fet, (see reference numerals 16C and 16D in box 16 of FIG. 3A).

2 ea. LM741, a general purpose operational amplifier (see reference numeral 14B in box 14 and reference numeral 18A in box 18 of FIG. 3A).

1 ea. MM740935, a CMOS digital voltmeter integrated circuit which includes a clock circuit with self-contained comparitor, and reference voltage (see reference numeral 26C in box 26 of FIG. 3B).

1 ea. DS74952, a MOS to LED hex digit driver (see reference numeral 26A in box 26 of FIG. 3B).

1 ea. NSB7881, a 0.7 inch LED quad digit display with common cathode (see reference numeral 28 of FIG. 3B).

2 ea. LM341P5, 3-terminal positive voltage regulator (see reference numerals 30 and 30A of FIG. 4).

1 ea. LM320MP-5, 3-terminal negative voltage regulator (see reference numeral 32 of FIG. 4).

Functionally similar second source integrated circuits from other manufacturers may also be used in the digital strength meter apparatus 8, if desired. FIGS. 3A and 3B also show resistors and capacitors external to the above designated IC's that are required for operation.

The load cell or force transducer 10 shown in FIGS. 1A, 2, and 3A generates an output from four gauges that are physically attached to the load cell 10 and electrically connected in a conventional four-arm Wheatstone bridge which has a nominal unstressed resistance of 350 ohms as measured across the bridge diagonals. The load cell 10 housed as shown in FIG. 1A is connected to U-shaped steel load shackles at each end thereof by means of threaded steel rods. A pair of handgrips which are shown in phantom form in FIG. 1A, are connected to the U-shaped load shackles.

Figure 4:
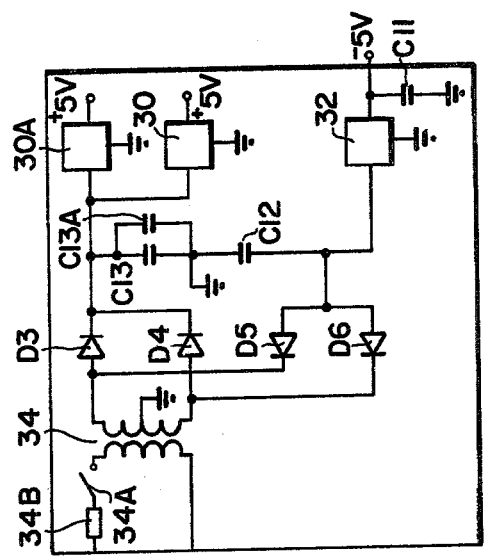
FIG. 4 is an electrical schematic diagram of the power supply used with the digital strength meter apparatus of FIG. 1.

The load cell (see FIG. 3A) is energized with ±10 volts from the +5 volt terminal of the LM341 voltage regulated supply 30A (see FIG. 4), and the −5 volt terminal of the LM320 voltage regulated supply 32 (see FIG. 4). Resistor R1 (see FIG. 3A) is preferably of 50 ohms and is connected in series with the +5 volt LM341 (30A of FIG. 4) and resistor R6 (see FIG. 3A) is preferably of 50 ohms and is connected in series with the −5 volt terminal of the negative voltage regulator 32. Resistors R1 and R6 both reduce the current through the load cell 10 by approximately 25% and also serve to further stabilize the Wheatstone bridge of the load cell 10. The load cell Wheatstone bridge potential input terminals are shunted by a series connection of resistor R2 (3 kilo-ohms), variable resistor R3 (1 kilo-ohm), Trimpot resistor R4 (3 kilo-ohms), and resistor R5 (3 kilo-ohms). Resistors R2 and R5 should preferably be 1% high stability metal film ⅛ watt types. The movable arm on the 3 kilo-ohms Trimpot resistor R4 is connected to one of the output load cell bridge terminals and also to one of the analog signal amplifier (12A in box 12) inputs through reversing switch 10A. The other output load cell bridge terminal is connected to the other analog signal amplifier (12A in box 12) input through the remaining unused terminal of reversing switch 10A. The function of the Trimpot resistor R4 is to balance the no load output of the load cell at the output of the LM725 analog signal amplifier 12A with variable resistor R3 being set at mid-range. The function of variable resistor R3 is to permit the unloaded output of the load cell 10 to be set to zero by knob 20 located in the front panel of the strength meter apparatus 8 shown in FIG. 1.

The LM725 analog signal amplifier 12A is driven in a differential mode from opposite non-potential output terminals of the Wheatstone bridge of the load cell 10 through 1 kilo-ohm ⅛ watt 1% metal film isolation resistors R7 and R8 which are connected to the inverting terminal 2 and the non-inverting terminal 3, respectively, of the LM725 analog signal amplifier 12A. The reversing switch 10A is placed in series with the LM725 analog signal amplifier(12A) input terminals so that the digital strength meter readout will always be up-scale or positive regardless of whether the load cell is operated in tension or compression. R9, a 50 kilo-ohm ⅛ Watt 1% metal film resistor, and C1, a 0.1 uf Mylar fixed capacitor, are connected from non-inverting op-amp terminal 3 of the operational amplifier 12A to ground. R12, a similar 50 kilo-ohm ⅛ Watt 1% metal film resistor, shunted by C2, a 0.1 uf Mylar fixed capacitor, is connected from op-amp inverting terminal 2 of the operational amplifier 12A to the output terminal 6. The output terminal 6 of the operational amplifier 12A is also connected to terminal 5 of the operational amplifier 12A through resistor R11 (39 ohms) and capacitor C4, which is a 0.02 uf fixed capacitor. Terminal 5 of the operational amplifier 12A is also connected to ground through 0.05 uf fixed capacitor C3 and resistor R10 (10 ohms). The effect of all the above designated RC networks of the operational amplifier 12A is to reduce the closed loop gain of the op-amp 12A to unity.

Output terminal 6 of the op-amp 12A is also coupled to non-inverting terminal 3 of the peak detector input amplifier 16C and to non-inverting terminal 3 of the analog chart recorder driver amplifier 14B and to non-inverting input terminal of the negative voltage detector amplifier 18A through diode D1 connected in the direction of anode to cathode. The cathode end of diode D1 is also connected to ground through a 100 uf tantalum capacitor C5. Diode D1 is shunted by resistor R13, a 510 kilo-ohm resistor. The cathode of diode D1 is also connected to resistor R14, a 1 kilo-ohm ⅛ Watt 1% metal film resistor which is in turn connected to resistor R15, a 10 kilo-ohm Trimpot resistor. One end of the Trimpot resistor R15 is connected to resistor R16, a 5 kilo-ohm ⅛ Watt 1% metal film resistor, the free end of which is grounded. The central terminal of the 10 kilo-ohm Trimpot resistor R15 is connected to terminal 11 of the (MM74C935) digital voltmeter (integrated circuit) 26 (see FIG. 3B) through a 100 kilo-ohm resistor R34. The non-inverting input terminal 3 of the amplifier 16D in the peak detector circuit 16 is also connected to the cathode of the diode D1 through a 1 kilo-ohm resistor R18. The non-inverting input terminal 3 of the amplifier 16D in the peak detector circuit 16 is also connected to the +5 volt terminal of the (LM341) voltage regulator 30 (see FIG. 4) through an 820 kilo-ohm resistor R23.

The operational amplifiers 16C and 16D are used in both the first and second stages of the peak detector circuit 16 in FIG. 3A and in box 16 of FIG. 2. Output terminal 6 of the input (LF355) 16C in the peak detector circuit 16 is connected to the anode of diode D2. The cathode of diode D2 is connected to inverting input terminal 2 of the input amplifier (LF355) 16C of peak detector circuit 16. The cathode terminal of diode 2 is also connected to one end of a 10 kilo-ohm resistor R19, the other end of which is connected to one end of a 5 kilo-ohm resistor R20, the other end of which is connected to the inverting input terminal 2 of the output amplifier (LF355) 16D in the peak detector circuit 16. Inverting input terminal 2 of the output amplifier (LF355) 16D in the peak detector circuit 16 is also connected to the −5 volt supply terminal 3 (LM320) the voltage regulator 32, in FIG. 4, through both a single pole, normally open switch 16B and a normally open push button switch 16A. The switches 16A and 16B are referred to above and are shown on the digital strength meter apparatus 8 of FIG. 1.

The common point between resistors R19 and R20 is connected to ground through capacitor C6, a 1 uf miniature capacitor. Balance control resistor R22 (a 10 kilo-ohm adjustable resistor) is connected between terminal 1 and terminal 5 of the output amplifier (LF355) 16D in the peak detector circuit 16. The variable center contact of the resistor R22 is connected to the +5 volt terminal of the (LM341) voltage regulator 30 (see FIG. 4) Output terminal 6 of the output op-amp (LF355) 16D in the peak detector circuit 16 is connected to pin 9 of (MM740935) the digital voltmeter integrated circuit 26 (see FIG. 3B) through a 1 kilo-ohm resistor R21.

Inverting terminal 2 of the (LM741) chart recorder amplifier 14B is connected to the output terminal 6 of the chart recorder amplifier 14B which is also brought to the external jack 14A (see FIG. 1B) to facilitate connection to a chart recorder (not shown).

The (LM741) operational amplifier 18A (in FIG. 3A) is used as the primary component of the negative output voltage detector circuit 18. The non-inverting input terminal 3 of the operational amplifier 18A of the negative output voltage detector circuit 18 is also connected to the cathode of the diode D1. The inverting input terminal 2 of the operational amplifier 18A of the negative output voltage detector circuit 18 is connected to the center arm of 10 kilo-ohm variable resistor R25 and to ground through a 250 ohm resistor R25A. One end of resistor R25 is connected to the +5 volt output terminal of (LM341) the voltage regulator 30 (see FIG. 4) through a 51 kilo-ohm resistor R24. The other end of resistor R25 is connected to the −5 volt output terminal of (LM320) the voltage regulator 32 (see FIG. 4) through a 51 kilo-ohm resistor R26. The output terminal 6 of the (LM741) negative output voltage detector 18A is connected to the base terminal of a 2N4354(PNP) decimal point driver transistor Q1 through a 1.5 kilo-ohm resistor R27 in box 24. The emitter terminal of the PNP transistor Q1 is connected to the +5 volt terminal of the voltage regulator 30 (see FIG. 4). The collector terminal of transistor Q1 is connected to the decimal point input terminal 8 on the (NSB7881) LED display 28 through a 43 ohm current limiting resistor R28.

The +5 volt terminal of the voltage regulator 30 (see FIG. 4) is also connected to terminal 1 of the (MM74C935) digital voltmeter integrated circuit 26C. The +5 volt output terminal of the voltage regulator 30 is also connected to the terminal 18 of the digital voltmeter integrated circuit 26C through a 3 kilo-ohm resistor R29. One end of 2 kilo-ohm resistor R30 is connected to resistor 29. The other end of the resistor R30 is connected to the terminals 15 and 25 of the digital voltmeter integrated circuit 26C. Terminal 19 of the digital voltmeter integrated circuit 26C is connected to resistor R30 through a 250 pf capacitor C7. Terminal 20 of the digital voltmeter integrated dircuit 26C is connected to capacitor C7 through an 8.2 kilo-ohm resistor R33. Terminal 17 of the digital voltmeter integrated circuit 26C is connected to terminal 14 of the digital voltmeter integrated circuit 26C through a 100 kilo-ohm resistor R31. Terminal 16 of the digital voltmeter integrated circuit 26C is also connected to the terminal 17 of the digital voltmeter integrated circuit 26C through a 1.2 kilo-ohm resistor R32. Terminal 14 of the digital voltmeter integrated circuit 26C is also connected to the terminals 15 and 25 of the digital voltmeter integrated circuit 26C through 0.47 uf capacitor C8. The terminals 15 and 25 of the digital voltmeter integrated circuit 26C are also connected to both terminal 11 of the digital voltmeter integrated circuit 26C through a 0.47 uf capacitor C9 and terminal 2 of the digital voltmeter integrated circuit 26C through a 10 uf tantalum capacitor C10. Terminals 21 through 24 of the digital voltmeter integrated circuit 26C are connected to the four inputs of a (DS754492 MOS to LED) hex digit driver 26A. The outputs of the hex digit driver 26A are connected to the four common digit cathodes (not shown) of the four digit (NSB7881) display 28. Terminals 3, 4, 5, 6, 26, 27 and 28 of the digital voltmeter circuit 26C are connected to the appropriate anode segments (seven are used for each digit) of the four digit display 28 through seven 43 ohm current limiting resistors R35 to R41.

FIG. 4 is a schematic diagram of the power supply used with the digital strength meter apparatus 8 of FIG. 1. Power transformer 34 is a Triad F-136XP unit with two 6.5 volt, 0.44 amp secondaries and a 115 volt primary. The power transformer 34 may also be another procuct of similar rating. The transformer 34 input is controlled by switch 34A and protected by a 0.5 amp fuse 34B. Diodes D3 to D6 are 1N4001 1 amp rectifiers connected in a dual center tap connection with a positive and a negative output. C13 and C13A are each 250 uf electrolytic capacitors connected from the positive unregulated voltage rail to ground. C12 is a 250 uf electrolytic capacitor connected from the unregulated negative voltage rail to ground. LM341 voltage regulator 30A has its +5 volt output used exclusively for the +5 volt supply to the load cell 10 (see FIG. 3). The voltage regulator 30 supplies +5 volts for all other requirements in the digital strength meter apparatus 8. In addition to the connections specifically shown in FIGS. 3A and 3B, +5 volts are supplied to terminal 7 of the op-amps 12A, 16C, 16D, 14B and 18A (see FIG. 3B). C11 is a 4.7 uf electrolytic capacitor connected from the output of the (LM320 MP-5) negative voltage regulator 32 to ground. The negative voltage regulator 32 supplies the negative voltage requirements of the load cell 10 (see FIG. 3A) as well as all other negative voltage inputs shown in FIGS. 3A and 3B of the digital strength meter apparatus 8. This includes connections to terminal 4 of opamps 12A, 16C, 16D, 14B and 18A and the common connection to switch 16B and push button 16A (see FIG. 3A).

BRIEF SUMMARY OF OPERATION

Adjustment of the 3 kilo-ohm Trimpot resistor R4 will balance the load cell output at terminal 6 of the analog signal amplifier 12A. This permits a zero adjustment of the digital readout means with the 1 kilo-ohm zero setting resistor R3 at its midpoint. Reversing switch 10A in FIGS. 2 and 3A would be used if, for example, a handgrip tester or evaluator is used whereby the load cell is operated in the compression mode. Adjustment of the 10 kilo-ohm resistor R25 in FIG. 3A sets the point at which the display decimal points are turned on. This control should be set so the decimal points come on with a very slight compression pressure on the load cell unit 10.

The output readout memory feature is a function of the time constant of C5 the 100 uf capacitor in the peak hold box 22 and C6 of 1 uf capacitor in the peak detector box 16 of FIG. 3A. Operation of either the normally open switch 16B or push button switch 16A (see FIG. 1), will cancel the stored readout thereby making the unit ready for a new series of strength measurements. The strength meter would be used in the memory mode of operation when a series of strength trials are being made by the same or several operators. The highest strength reading is scored in the display 28 and retained in the memory. The memory would be switched off when the digital strength meter apparatus 8 is used in a series of exercises to achieve consecutive uniform, but not necessarily maximum readings, to a desired or assigned level.

Adjustment of 10 kilo-ohm adjustable resistor R22 is used to set the output at terminal 6 of the peak detector 16D equal to zero. The 10 kilo-ohm Trimpot resistor R15 is used to permit calibration of the output of the digital voltmeter integrated circuit 26C so that one pound of force on the load cell 10 equals one digit on the readout or display 28.

While the invention has been particularly shown and described in reference to the preferred embodiment thereof, it will be understood by those skilled in the art that changes in the form and details may be made without departing from the spirit and scope of the invention.

What is claimed is:

1. A digital strength meter apparatus for measuring human strength comprising, in combination, means for converting each one of an applied human compressive and human tensive force to an electrical signal, gripping means coupled to said converting means for applying said force to said converting means, peak detector means electrically coupled to said converting means for retaining a signal representative of the maximum force applied to said gripping means, and digital readout means electrically coupled to said peak detector means for digitally displaying in units of force per digit unit the peak force applied to said converting means by said gripping means.

2. A digital strength meter apparatus in accordance with claim 1 wherein said means for converting an applied force to an electrical signal comprises a load cell.

3. A digital strength meter apparatus in accordance with claim 1 wherein said gripping means comprises at least one handgrip member.

4. A digital strength meter apparatus in accordance with claim 3 wherein said gripping means comprises two handgrip members.

5. A digital strength meter apparatus in accordance with claim 4 wherein said means for converting an applied force to an electrical signal comprises a load cell.

6. A digital strength meter apparatus in accordance with claim 1 wherein said converting means comprises amplifier means for amplifying said electrical signal, and said digital readout means comprises digital voltmeter means coupled to said amplifier means for converting the amplified signal received from said amplifier means from an analog signal to a digital signal.

7. A digital strength meter apparatus in accordance with claim 6 including analog electrical output means coupled to said amplifier means for driving a strip chart graphic recorder.

8. A digital strength meter apparatus in accordance with claim 6 including means for adjusting the zero point of said digital readout means.

9. A digital strength meter apparatus in accordance with claim 1 wherein said peak detector means comprises switching means for cancelling the digital readouts displayed by said digital readout means.

* * * * *